United States Patent [19]

Butterworth et al.

[11] 4,112,153

[45] Sep. 5, 1978

[54] METHOD OF CONTROLLING WATER REPELLENCY IN NON-WOVEN FABRIC

[75] Inventors: George A. M. Butterworth, Western Springs; Frank Fillwalk, Oak Lawn, both of Ill.

[73] Assignee: Johnson & Johnson, New Brunswick, N.J.

[21] Appl. No.: 783,928

[22] Filed: Apr. 4, 1977

[51] Int. Cl.$^2$ .................... A61F 13/16; D21H 1/34
[52] U.S. Cl. .................... 427/390 E; 34/41; 128/284; 128/285; 128/287; 128/290 P; 128/290 R; 156/305; 427/392; 427/391
[58] Field of Search .......... 427/390 E, 394, 391, 427/392; 128/284, 285, 287, 290 P, 290 R; 156/305; 34/41

[56] References Cited

U.S. PATENT DOCUMENTS

| 3,683,916 | 8/1972 | Mesek et al. | 128/287 |
| 3,730,184 | 5/1973 | Mesek | 128/287 |
| 3,837,343 | 9/1974 | Mesek | 128/287 |
| 3,965,904 | 6/1976 | Mesek et al. | 128/287 X |

Primary Examiner—Michael R. Lusignan

[57] ABSTRACT

A method is provided for increasing the water-repellency of a normally water-wettable, bonded, non-woven fabric bearing a surfactant selected from the group consisting of non-ionic surfactants and anionic surfactants. The method comprises heating a selected region of the fabric to an elevated temperature at which the surfactant is unstable, and maintaining the region at the elevated temperature for a time period sufficient to denature the surfactant without damaging the fabric.

21 Claims, 5 Drawing Figures

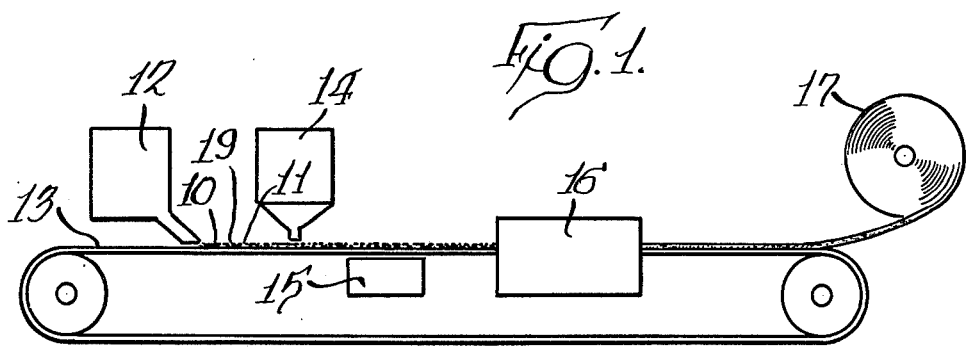
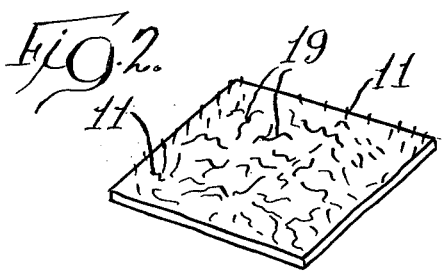
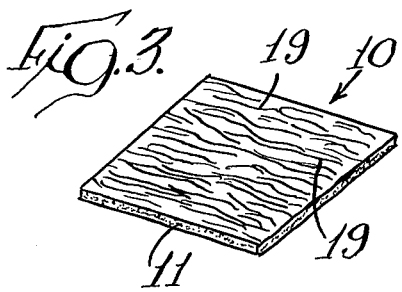
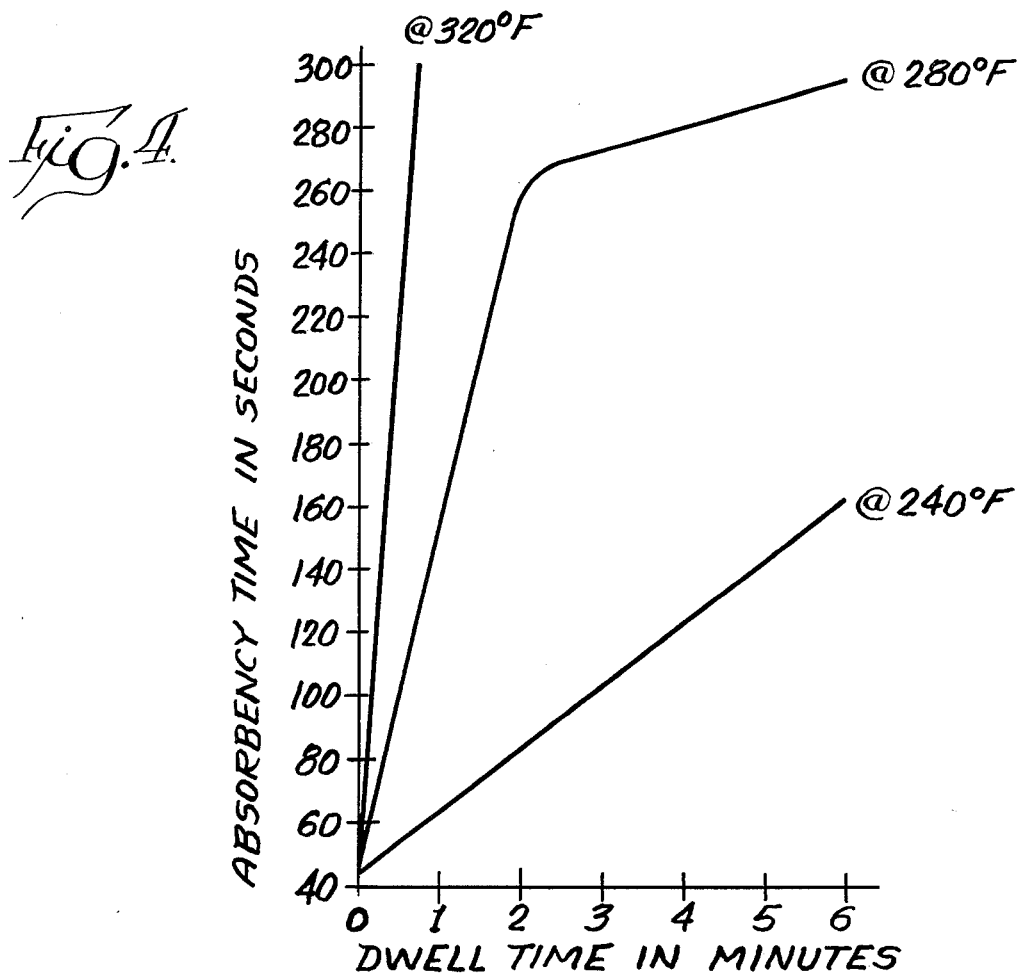

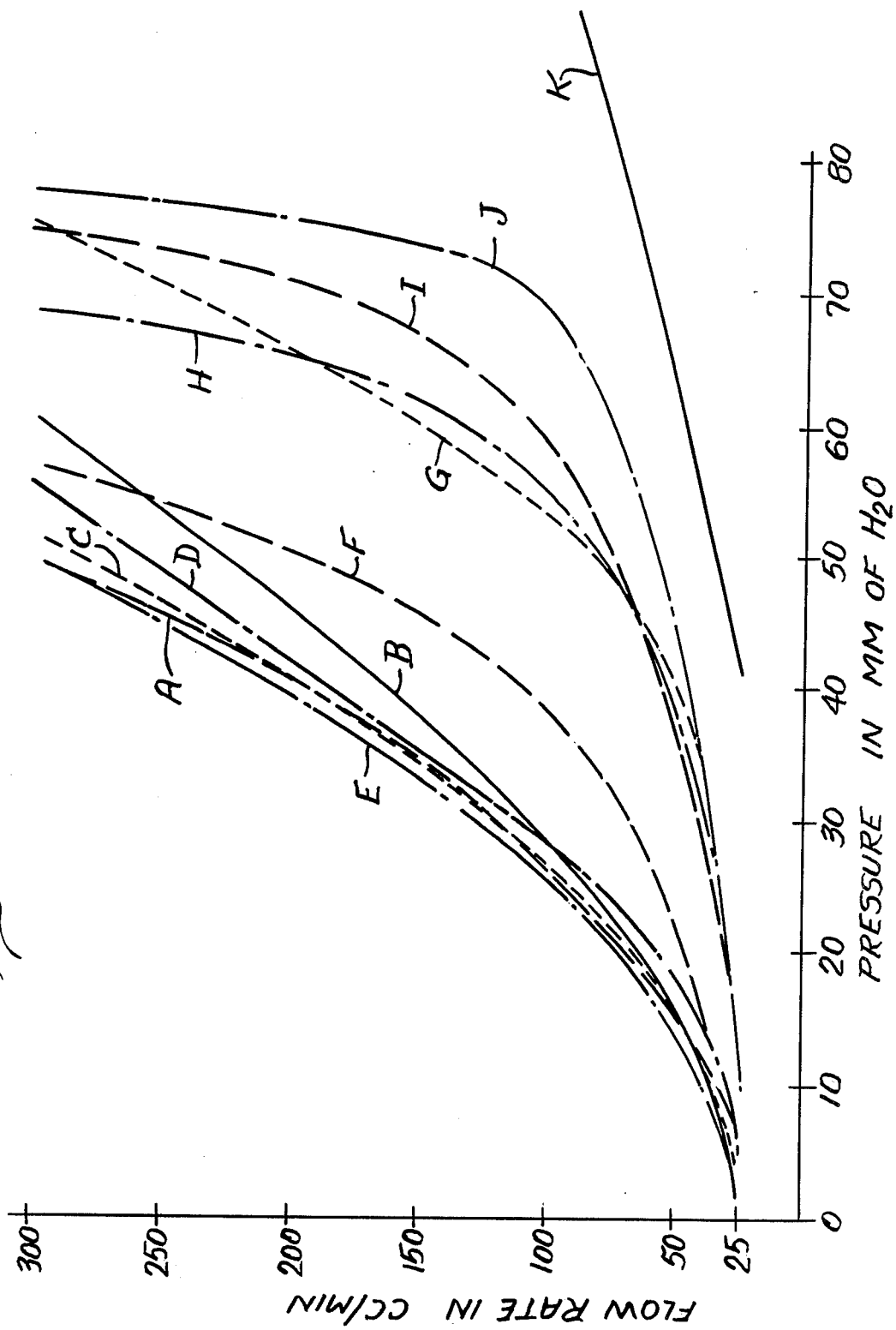

METHOD OF CONTROLLING WATER REPELLENCY IN NON-WOVEN FABRIC

BACKGROUND OF THE INVENTION

This invention relates to a method of increasing the water repellency of water-wettable, bonded, non-woven fabrics bearing a surfactant.

Disposable diapers have been well accepted by consumers because they provide substantial advantages from the standpoint of convenience. Most disposable diapers incorporate three basic elements into their construction: a water impervious backing sheet, a water-permeable facing sheet, and an absorbent cellulosic batt situated between the facing sheet and the backing sheet.

One advantage which disposable diapers may have over non-disposable cloth diapers is that the multilayer disposable diaper, such as the diaper disclosed in U.S. Pat. No. 3,612,055 to Mesek et al., may be constructed so that when an infant voids into the diaper, the absorbent batt layer will absorb and retain the urine, while the facing sheet which is situated next to the infant's skin remains dry. To accomplish this result, the facing sheet must be less wettable than the absorbent batt. However, the facing sheet must be wettable, as opposed to being water repellent, since a water repellent facing sheet could undesirably impede or prevent the penetration of excreted body fluids through the facing sheet and into the absorbent layer or layers behind it.

It is commercially advantageous to construct the facing sheet from short-length cellulosic fibers, such as fibers of wood pulp or cotton linters, as is disclosed in U.S. Pat. No. 3,633,348 to Liloia et al. Facing sheets constructed in accordance with this patent are less expensive than facing sheets made from woven fabrics, and thus are better suited for use in disposable diapers.

The method of preparing the bonded, non-woven facing sheet disclosed in U.S. Pat. No. 3,633,348 to Liloia et al. includes the steps of forming a web of randomly laid dry fibers, impregnating the web with a binder and a surfactant, and drying the web to form the facing sheet. The surfactant is included in the step of impregnating the web with the binder in order to offset the water-repellency which the binder imparts to the normally cellulosic fibers. To optimize diaper performance, it would be desirable to control the wettability of the diaper facing so that some areas or regions of the diaper facing are more wettable than other areas or regions thereof.

U.S. Pat. No. 3,730,184 to Mesek discloses a method for preparing a non-woven facing sheet having a controlled degree of wettability in which the central portion of a web of randomly laid dry fibers is treated with a binder and a surfactant while the marginal portions of the web are treated with binder material alone. Facing sheets which are products of this method have marginal portions which are substantially water repellent, due to the repellency imparted to the fibers by the binder, and central portions which are substantially water absorbent. However, the degree to which the wettability of different regions of a diaper may be controlled is limited by the configuration of the apparatus for distributing the surfactant and binder-containing solutions.

SUMMARY OF THE INVENTION

The present invention provides a method for increasing the water repellency of a selected region of a normally water-wettable, bonded, non-woven fabric which bears a heat-unstable surfactant selected from the group consisting of a non-ionic or an anionic surfactant or a mixture thereof. The method comprises heating the selected region of the fabric to an elevated temperature at which the surfactant is unstable, and maintaining the selected fabric region at the elevated temperature for a time period sufficient to denature the surfactant thereon without damaging the fabric. One aspect of this invention relates to a method of preparing a bonded, non-woven fabric having a controlled degree of wettability comprising: forming a web of randomly laid dry fibers; impregnating the web with a liquid binder composition which includes a heat-unstable surfactant which is a member of the group consisting of a non-ionic surfactant, an anionic surfactant, and mixtures thereof; drying the web to form a water-wettable, bonded, non-woven fabric; heating a selected region of the fabric to an elevated temperature at which the surfactant is unstable; and maintaining the selected region of the fabric at the elevated temperature for a time period sufficient to denature the surfactant without damaging the fabric, thereby increasing the water repellency of the selected fabric region.

The method of the present invention provides an inexpensive and convenient method of controlling the level of water repellency of facing sheets manufactured, for example, in accordance with the method provided in U.S. Pat. No. 3,633,348 to Liloia et al. By controlling the temperature and the duration of time to which the selected regions of the surfactant-bearing fabric are exposed to an elevated temperature, it is possible to manufacture conveniently facing sheets having a predetermined level or pattern of water repellency which level or pattern may be controlled to a high degree.

BRIEF DESCRIPTION OF THE DRAWINGS

FIG. 1 is a schematic view illustrating the practice of the present invention;

FIG. 2 is a perspective view illustrating a swatch of fabric of the present invention;

FIG. 3 is a perspective view illustrating a modification of the fabric of the present invention;

FIG. 4 is a plot of the absorbency time in seconds as a function of the dwell time of identical fabric samples placed in a heated environment at a controlled temperature; and FIG. 5 is a plot of the flow rate of water as a function of the wetting through pressure of the water for test samples of fabric which had been exposed to different heated environments for different lengths of time.

DETAILED DESCRIPTION

Non-woven fabrics which are suitable for use as facing sheets in disposable diapers and similar absorbent products have a fiber content which is predominantly short fibers. The term "short fibers" is defined as wood pulp, cotton linters, or the like, where the fibers are less than one-quarter inch in length. Suitably, the short fibers comprise about 75 to about 98 percent of the total fiber content of the non-woven fabric, the balance being textile length fibers such as rayon.

Typical facing sheet materials made from bonded, nonwoven fabrics have fabric weights in the range of about 1 to 5 oz./yd.$^2$ and densities of less than 0.15 g./cc., generally in the range of about 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers. Fabrics of this general type are prepared by first forming a web of randomly laid dry fibers, the web when laid having a density of about 0.09 g./cc. to 0.025 g./cc. measured by ASTM Method D-1777 at 0.16 lbs./in.$^2$ (test procedure set forth in the manual of *The American Society for Testing Materials*). Where wood pulp fibers are used, the same are generally obtained in the form of a fiberboard of fairly dense construction from which the fibers must be separated. These wood pulp fibers generally have a fiber length ranging from a fine dust to about one-quarter inch.

Short-length fibers are best classified by the Clark Classification procedure described in the test manual of *The Technical Association of Pulp and Paper Industry* (TAPPI - T233 SU64). The web is then impregnated with a binder by flowing a solution or dispersion of the binder through the web. The impregnated web is then subjected to suction to remove excess binder and assure uniform distribution of binder throughout the fiber web. This impregnation by binder followed by suction is hereinafter referred to as suction-bonding. The fiber web at this point has, on a solids basis, 7 to 9 percent dry solids add-on by weight of the web. Depending upon the strength requirements of the web, the loft and the softness desired in the end product, the range of dry solids added on may vary over the range of about 1 to about 30 percent. The web so formed is then dried and heated to cure the binder. This can be done simultaneously by passing into a drying oven heated to a temperature of about 310° to 320° F. where the same is dried and the binder cured. The preferred binders are of the self-curing acrylic latex family, the urethane family, or other binders which can be utilized in low viscosity solutions or suspensions. The general method of manufacturing bonded, non-woven fabrics is shown in U.S. Pat. No. 3,663,348 to Liloia et al.

The facing sheet may also be made of an apertured, non-woven fabric which is formed, for example, in accordance with the teachings of commonly assigned U.S. Pat. Nos. 2,862, 251 to Kalwaites, 3,081,514 to Griswold and 3,081,515 to Griswold et al. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder is utilized to help retain the fibers in their prearranged locations, as is also well known to those skilled in the art. The fabric can be made of naturally occurring fibers, synthetic fibers, or blends thereof. Typical facing sheets made of a polyester type material can have a weight of about 0.75 oz./yd.$^2$ To facilitate the distribution of the binder throughout the non-woven web as well as to enhance the wettability of the ultimately produced fabric, a non-ionic or anionic surfactant is incorporated into the aforementioned low viscosity binder solutions or suspensions. However, when the bonded, non-woven fabric is incorporated into an absorbent product as a facing sheet therefor, it is desirable to reduce the wettability of the facing sheet in certain predetermined areas or regions, for example, around the margins of the absorbent product, so as to contain the absorbed body fluids within the absorbent product. Also, in some instances it is desirable to reduce the inherent wettability of the facing sheet in order to provide a relatively dry facing next to the wearer's skin which facing is nevertheless moisture permeable.

To this end, the present invention provides a convenient method for controlling the wettability of a bonded, non-woven fabric. Initially, bonding of the fabric is achieved by using a binder solution or suspension containing a surfactant that can be denatured, or even degraded at elevated temperatures that are low enough (usually below about 600° F.) so as to have no detrimental effect on the fabric itself or on the binder that is present. Next, the produced fabric is subjected to a heat treatment so that in predetermined areas or regions of the fabric the surfactant that is present is denatured to provide the desired degree of hydrophobicity.

The practice of the present invention is illustrated schematically in FIG. 1. A web 10 of mixed randomly disposed short fibers 11 and long fibers 19 are deposited from fiber-laying equipment 12 onto a foraminous moving screen or belt 13. The fiber-laying equipment 12 is preferably of the air deposition type such as a modified RANDO WEBBER made by the Curlator Co. The low density fiber web 10 is moved by belt 13 below a screen containing a weir box 14 of a liquid binder composition with the binder being present in the solution or as an aqueous dispersion. Suitable binders are of the self-curing acrylic latex family, or other binders which can be utilized in low viscosity solutions or suspensions which preferably have viscosities of less than about 5 centipoises.

The surfactant present in the binder composition can be a non-ionic surfactant and/or an anionic surfactant that is heat-unstable, i.e., heat-denaturable. A suitable anionic surfactant for use in the method of the present invention is a water soluble salt of an ester of an alkane dicarboxy sulfonate, such as the sodium salt of dioctyl-sulfosuccinate, which is commercially available under the designation "Aerosol OT" from American Cyanamid Co., Wayne, N.J. Other suitable anionic surfactants are the sodium salts of alkylaryl polyether sulfates such as the sodium octylphenoxy alkyl sulfate commercially available under the designation "Triton W30," and also the sodium salts of the alkylaryl polyether sulfate commercially available under the designation "Triton 7-70" (denatures at a temperature below about 140° C.), both from Rohm & Hass Co., Philadelphia, Pa.

Suitable non-ionic surfactants are the non-ionic polyoxyalkylene derivatives of a partial long chain fatty acid ester, an example of which is a polyoxyalkylene derivative of sorbitan monolaurate. Particularly preferred is polyoxyethylene (20) sorbitan monolaurate, commercially available under the designation "Tween 20" from ICI United States, Inc., Atlas Chemicals Div., Wilmington, De. Also suitable are the non-ionic aliphatic polyethers such as the aliphatic polyether commercially available under the designation "Discopen No. 205" (denatures at about 121° C. to about 130° C.) from Dixie Size & Chemicals Company.

Other suitable surfactants are the non-ionic surfactants commercially available under the designation "Sulfanole 550" from Sun Chemical Co., New York, N.Y. and commercially available under the designation "Mykon NRW-3."

The surfactant-bearing binder fluid is flowed onto and through the web 10 in quantities substantially in excess of the ultimate amount to be deposited on the fibers completely impregnating the web. The web 10, immediately after impregnation with the binder solution, passes over a suction box 15 where excess binder is removed. The impregnated web 10 is then conveyed by belt 13 to a curing station such as a dryer 16. The fabric is then removed from belt 13 and collected, for example, on fabric roll 17. A section of fabric so formed is illustrated, for example, in FIG. 2 of the drawings showing a very small percentage of long fibers 19. An alternate construction with a larger percentage of long fibers 19 is shown diagrammatically in FIG. 3.

The binder, in the preferred method of manufacture, is flowed onto the fabric from the weir box 14 and a major portion thereof is withdrawn in the suction box 15 before the fabric enters the dryer 16. It is important in attaining the lofty and soft character of the fabrics made hereunder that the application, removal and drying of the binder be without substantial compression of the fabric.

To obtain the desired level of wettability of the facing sheet, preselected portions of the surfactant-bearing fabric are subjected to a heat treatment at an elevated temperature for a period of time sufficient to denature and/or degrade the surfactant without damaging the fabric. The heat-treating temperature is in the range of about 240° F. to about 600° F., and even more preferably is maintained at a temperature in the range of about 280° F. to about 400° F. Typical dwell times for surfactant denaturization are in the range of about 10 to about 100 seconds, and preferably, about 20 to about 60 seconds.

A particular advantage of the present invention is that is provides a convenient method for controlling the wettability characteristics of the facing sheet in an absorbent product to a high degree. Another distinct advantage of the method of the present invention is that different degrees of wettability may be provided in different areas of the surfactant-bearing facing sheet by exposing different areas on the facing sheet to different degrees of heat for different periods of time. In general, the water repellency of any area of the fabric may be increased by either elevating the temperature of that portion of the fabric to a higher degree, or by increasing the time the fabric is maintained at the elevated temperature, or any combination of the two.

In some instances, e.g., when the surfactant is a nonionic polyoxyalkylene derivative of a partial long chain fatty acid ester, the heat-induced denaturation of the surfactant can be speeded up by the use of an oxidizing agent such as a peroxide, a permanganate, or the like, in contact with the surfactant carried by the web. Particularly preferred oxidizing agent for this purpose is hydrogen peroxide. The oxidizing agent can be added to the binder fluid during web manufacture or can be applied to the web or to selected portions thereof as desired.

The present invention is further illustrated by the following examples.

EXAMPLE 1

Several identical samples were prepared from two-ply, air-laid, rayon-rich fabric containing about 75 weight-percent wood pulp ("Alphanier" pulp) and about 25 weight percent of crimped, semi-dull viscose rayon fiber (1½ denier, 1½ inches long). The fabric was bonded using as a binder solution a polyacrylate emulsion ("Hycar 2600 × 120" commercially available from B. F. Goodrich Chemical Co., Akron, Ohio) containing ammonium chloride as catalyst, "Tween 20" as the surfactant, and an antifoam ("Drew Y629", commercially available from PVO International, Inc., Boonton, N.J.). The binder solution had a solids content of about 6 weight-percent, the binder solution pickup was about 150 weight percent, and the dry binder solids add-on was about 9 weight percent. The samples were placed in three ovens which were separately maintained at 320° F., 280° F. and 240° F. for three different time periods.

To test the absorbency of the fabric, three inch diameter pieces were cut from several of the samples, and were clamped across a horizontal 2 inch diameter hole beneath the fabric. Water was then flowed into the hole at a specified rate, and the pressure which developed at the interface of the liquid in contact with the underside of the fabric was controlled so that the pressure never exceeded a preset amount. The time for the water to pass through the fabric (the absorbency time) was then measured and taken as an indication of the fabric's wettability.

Table 1 shows the "dwell time" or the length of time the samples were left in the ovens and the effect of the different temperature exposure and dwell time on the fabric's absorbency time.

TABLE 1

| Sample No. | Oven Temp. (° F.) | Dwell Time (Sec.) | Absorbency Time (Sec.) |
|---|---|---|---|
| 1(Control) | 0 | 0 | 43 |
| 2 | 240 | 20 | 43 |
| 3 | 280 | 20 | 55 |
| 4 | 320 | 20 | 155 |
| 5 | 240 | 40 | 53 |
| 6 | 280 | 40 | 93 |
| 7 | 320 | 40 | 300 |
| 8 | 240 | 60 | 66 |
| 9 | 280 | 60 | 143 |
| 10 | 240 | 120 | 85 |
| 11 | 280 | 120 | 281 |
| 12 | 240 | 240 | 121 |
| 13 | 280 | 240 | 275 |
| 14 | 240 | 360 | 162 |
| 15 | 280 | 360 | 295 |

FIG. 4 is a plot of the absorbency time in seconds as a function of the dwell time of identical fabric samples in a heated environment, showing the effect on the absorbency time as the dwell time was increased in heated environments at three different temperatures. As the dwell time, the temperature, or both the temperature and dwell time increased, the time for the water to pass through the fabric (or the absorbency time) increased, indicating that the wettability of the fabric has been decreased. From this data, suitable temperature and exposure times can be selected for the oven or heating means to produce a fabric having a controlled degree of wettability. Although variations of the amount of the surfactant in the binder solution, the amount of binder solution removed from the impregnated low density fiber web, and the type of surfactant used will affect the dwell time and temperature curves shown in FIG. 4; the dwell time and temperature exposures needed to give the desired degree of water absorbency may be easily determined as set forth above.

EXAMPLE 2

Several samples of identically bonded, non-woven fabrics were prepared and tested as in Example 1; however, the flow rate through the fabric was adjusted to a constant value and the wetting through pressure was measured for each of the controlled flow rates. The "wetting through pressure" is the pressure necessary to force the liquid through the fabric. Generally, a lower wetting through pressure indicates good wettability, while a higher pressure indicates poor wettability, for the same fabric structure, composition and fiber organization. The results are summarized in Table 2, below, and in FIG. 5, which is a plot showing the flow rate as a function of wetting through pressure for each of the test samples listed in Table 2.

TABLE 2

Influence of Heat Treatment Upon Bonded SPP Fabric Wetting Through Properties

| Sample Number | Heat History | Wetting Through Pressure at Specified Flow Rate mms Saline | | |
|---|---|---|---|---|
| | | 25 cc/min | .50 cc/min | 100 cc/min |
| 20 | 3 sec. Metal Tech at 240° F. | 2.0 | 13.3 | 25.2 |
| 21 | Control-Air Dried No Heat Treatment | 3.3 | 18.2 | 25.2 |
| 22 | 3 sec. Metal Tech at 280° F. | 4.2 | 13.7 | 27.7 |
| 23 | 8 sec. Metal Tech at 285° F. | 6.3 | 18.2 | 23.0 |
| 24 | 8 sec. Metal Tech at 240° F. | 8.1 | 19.0 | 27.8 |
| 25 | 3 sec. Metal Tech at 320° F. | 4.5 | 21.9 | 38.2 |
| 26 | 3 sec. Metal Tech at 400° F. | 9.2 | 41.8 | 53.5 |
| 27 | 3 sec. Metal Tech at 360° F. | 19.2 | 38.0 | 55.4 |
| 28 | 8 sec. Metal Tech at 360° F. | 15.2 | 34.8 | 58.9 |
| 29 | 8 Sec. Metal Tech at 400° F. | 13.8 | 40.3 | 69.1 |
| 30 | 120 sec. in oven at 320° F. | 40.8 | 62.2 | 98.2 |

We claim:

1. A method of increasing water-repellency of a selected region of a normally water-wettable, bonded, non-woven fabric bearing a heat-unstable surfactant selected from the group consisting of a non-ionic surfactant, an anionic surfactant and mixtures thereof which comprises heating the selected region of the fabric to an elevated temperature at which the surfactant is unstable, and maintaining the selected fabric region at the elevated temperature for a time period sufficient to denature the surfactant thereon without damaging the fabric.

2. The method of claim 1 wherein the anionic surfactant is a water-soluble salt of an ester of an alkane dicarboxy sulfonate.

3. The method of claim 1 wherein the non-ionic surfactant is polyoxyalkylene derivative of a partial long chain fatty acid ester.

4. The method of claim 1 wherein the surfactant is a sodium salt of dioctylsulfosuccinate.

5. The method of claim 1 wherein the surfactant is polyoxyethylene (20) sorbitan monolaurate.

6. The method of claim 1 wherein the surfactant is a polyoxyalkylene derivative of sorbitan monolaurate.

7. The method of claim 1 wherein the selected region of the surfactant-bearing fabric is heated to a temperature of about 240° F. to about 600° F.

8. The method of claim 7 wherein the selected region is maintained at said elevated temperature for about 10 to about 100 seconds.

9. The method of claim 7 wherein the selected region is maintained at said elevated temperature for about 20 to about 60 seconds.

10. The method of claim 1 wherein the selected region of the surfactant-bearing fabric is heated to an elevated temperature in the range of about 280° F. to about 400° F.

11. The method of claim 10 wherein the selected region is maintained at said elevated temperature for about 10 to about 100 seconds.

12. The method of claim 10 wherein the selected region is maintained at said elevated temperature for about 20 to about 60 seconds.

13. A method of preparing a bonded, non-woven fabric having a controlled degree of wettability comprising;
forming a web of randomly laid dry fibers,
impregnating the web with a liquid binder composition which includes a heat-unstable surfactant which is a member of the group consisting of a non-ionic surfactant, an anionic surfactant, and mixtures thereof,
drying the web to form a water-wettable, bonded, non-woven fabric,
heating a selected region of the fabric to an elevated temperature at which the surfactant is unstable, and maintaining the fabric at the elevated temperature for a time period sufficient to denature the surfactant without damaging the fabric, thereby increasing the water repellency of the selected fabric region.

14. The process of claim 13 wherein at least 75 percent of the fibers are less than ¼ inch in length.

15. The process of claim 13 wherein from about 75 percent to about 98 percent of the fibers are less than ¼ inch in length.

16. The process of claim 13 wherein the binder composition has a viscosity of less than about 5 centipoises.

17. The method of claim 13 wherein the surfactant is selected from the group consisting of a water-soluble salt of an ester of an alkane dicarboxysulfonate and a non-ionic polyoxyalkylene derivative of a partial long chain fatty acid ester.

18. The method of claim 13 wherein at least one portion of the surfactant-bearing fabric is placed in a hot environment maintained at a temperature of about 240° F. to about 600° F. for a time of about 10 to about 100 seconds.

19. The method of claim 13 wherein at least one portion of the surfactant-bearing fabric is placed in a hot environment maintained at a temperature of about 280° F. to about 400° F.

20. The method in accordance with claim 13 wherein said heat-unstable surfactant is contacted with an oxidizing agent before said selected region of the fabric is heated.

21. The method in accordance with claim 20 wherein said heat-unstable surfactant is a non-ionic polyoxyalkylene derivative of a partial long chain fatty acid ester and wherein the oxidizing agent is hydrogen peroxide.

* * * * *